United States Patent
Van Antwerp et al.

(10) Patent No.: US 6,594,156 B1
(45) Date of Patent: Jul. 15, 2003

(54) DEVICE AND METHOD FOR CIRCUIT PROTECTION DURING RADIATION STERILIZATION

(75) Inventors: William P. Van Antwerp, Valencia, CA (US); Sheana Karre, Lincoln, NE (US); Adrian Prokop, Woodinville, WA (US); Sara Akiko Stinson, Alameda, CA (US); Jason Fong, Pleasant Hill, CA (US); James J. Rosenberg, Monrovia, CA (US)

(73) Assignee: MiniMed Inc., Sylmar, CA (US)

( * ) Notice: Subject to any disclaimer, the term of this patent is extended or adjusted under 35 U.S.C. 154(b) by 0 days.

(21) Appl. No.: 09/556,227

(22) Filed: Apr. 24, 2000

(51) Int. Cl.[7] .......................... H05K 9/00; H01L 23/552
(52) U.S. Cl. ..................... 361/816; 361/800; 174/35 R; 174/35 MS; 250/505.1; 250/515.1; 53/425; 257/659
(58) Field of Search ................................. 361/752, 800, 361/814, 816; 174/35 R, 35 MS; 206/438; 53/425; 250/505.1–515.1; 257/659, 666

(56) References Cited

U.S. PATENT DOCUMENTS

| | | | | |
|---|---|---|---|---|
| 4,652,763 A | * | 3/1987 | Nablo .................. 250/492.3 |
| 4,814,943 A | * | 3/1989 | Okuaki .................. 174/52.2 |
| 4,833,334 A | * | 5/1989 | Valy et al. ................ 250/515.1 |
| 4,975,762 A | * | 12/1990 | Stradley et al. ............. 257/660 |
| 5,014,494 A | * | 5/1991 | George ........................ 53/425 |
| 5,250,257 A | * | 10/1993 | Lengfelder ................... 422/22 |
| 5,397,735 A | | 3/1995 | Mercandalli et al. .......... 437/83 |
| 5,406,117 A | * | 4/1995 | Dlugokecki et al. ......... 257/659 |
| 5,496,302 A | | 3/1996 | Minshall et al. ............. 604/410 |
| 5,635,754 A | * | 6/1997 | Strobel et al. ............... 257/659 |
| 5,737,191 A | * | 4/1998 | Horiuchi et al. ............. 361/764 |
| 5,750,926 A | * | 5/1998 | Schulman et al. ........... 174/52.3 |
| 5,825,042 A | * | 10/1998 | Strobel et al. ............. 250/515.1 |
| 5,847,938 A | * | 12/1998 | Gammon ..................... 361/816 |
| 5,881,534 A | * | 3/1999 | Ahlqvist et al. ............... 53/403 |
| 5,889,316 A | * | 3/1999 | Strobel et al. ............. 250/515.1 |
| 5,896,267 A | * | 4/1999 | Hittman et al. .............. 361/302 |
| 5,939,772 A | * | 8/1999 | Hurst et al. .................. 257/659 |
| 5,973,263 A | * | 10/1999 | Tuttle et al. ................ 174/52.2 |
| 6,255,719 B1 | * | 7/2001 | Kuriyama et al. ............ 257/659 |
| 6,261,508 B1 | * | 7/2001 | Featherby et al. ............ 264/105 |

FOREIGN PATENT DOCUMENTS

| | | | |
|---|---|---|---|
| EP | 1529968 | 10/1978 | .......... H01L/23/56 |
| WO | 9834451 | 8/1998 | ............ H05K/9/00 |

* cited by examiner

Primary Examiner—Jayprakash N. Gandhi
(74) Attorney, Agent, or Firm—Gates & Cooper LLP

(57) ABSTRACT

A circuit protection device for protection of sensitive components during high energy radiation sterilization that includes a support substrate and a protective housing. The substrate supports the sensitive components. The protective housing is hermetically coupled to the support substrate to seal the sensitive components within the protective housing. Preferably, the protective housing stops high energy used in the high energy sterilization from damaging the sensitive components from a predetermined exposure level of high energy sterilization. The circuit protection device may further include a protective conductor that is coupled to the support substrate on a side which is opposite the protective housing to prevent high energy from entering the opposite side of the support substrate. The circuit protection device can also include an energy absorbing material contained within an area sealed by the protective housing to absorb high energy by products produced by the protective housing stopping the high energy used in the high energy sterilization. Preferably, the support substrate is a circuit board, and the sensitive elements are semiconductors. Also, the high energy sterilization is E-beam sterilization and the high energy are electrons, and the high energy byproducts are x-rays.

28 Claims, 10 Drawing Sheets

| TEST # | DIGIKEY # | MANUF. # | MANUF. | UNIT PRICE | DESCRIPTION | PACKAGE | Vcco (V) | Ic (mA) | hfe MIN/MAX | Ic(mA)/Vce(V) |
|---|---|---|---|---|---|---|---|---|---|---|
| 03 | 2SC5019-ND | 2SC5019 | PANASONIC | - | NPN Si UHF | MINI POWER (SC-62) | 10 | 80 | 80/250 | 20/8 |
| -- | ZDT758TA | ZDT758 | ZETEX | $1.50 (Q=100) | DUAL PNP MEDIUM POWER | SM-8 | -400 | -500 | 50/-- | -1/-5 |
| 04 | BCX70KCT-ND | BCX70 | ZETEX | $0.12 (Q=1000) | NPN Si SMALL SIGNAL - HIGH BETA | SOT-23 | 45 | 200 | 100/630 | 0.01/5 |
| 07 | PN4888-ND | 2N5401 | FAIRCHILD | $0.08 (Q=10000) | PNP - LOW BETA, HIGH VOLTAGE | TO-92 | -150 | -10 (OR -200) | 50/240 | 1/-5 |
| 01 | BF621CT-ND | BF621 | ZETEX | $0.39 (Q=500) | PNP Si HIGH VOLTAGE - LOW BETA | SOT-89 | -300 | -50 | 50/-- | -25/-20 |
| 02 | XN4401CT-ND | XN4401 | PANASONIC | $0.11 (Q=1000) | ARRAY PNP/PNP | MINI-6P (SC-74) | -50 | -100 | 160/460 | -2/-10 |
| 06 | XN4501CT-ND | XN4501 | PANASONIC | $0.11 (Q=1000) | ARRAY NPN/NPN | MINI-6P (SC-74) | 50 | 100 | 160/460 | 2/10 |
| 05 | XN2501CT-ND | XN2501 | PANASONIC | $0.11 (Q=1000) | ARRAY NPN/NPN BASE-COUPLED | MINI-5P (SC-74A) | 50 | 100 | 160/460 | 2/10 |

FIG. 4

CRITERIA FOR CHOICES:
- PNP vs. NPN
- LOW vs. HIGH BETA
- LOW vs. HIGH VOLTAGE

| PARAMETER | B/A | 1 | 2 | 4 | 5 | 6 | |
|---|---|---|---|---|---|---|---|
| BF (PEAK) | B | 80.4 | 218 | 490 | 232 | 300 | 112 |
| | A | 57 | 85.2 | 228 | 122 | 116 | 43.2 |
| B @ ~ 100 uA | B | 80.4 | 218 | 490 | 232 | 300 | 112 |
| | A | 44.3 | 15.8 | 33.4 | 30.5 | 29.5 | 8.94 |
| IS (A) | B | -1.28E-14 | -9.54E-15 | 3.19E-14 | 1.05E-14 | 1.82E-14 | -1.30E-14 |
| | A | -1.28E-14 | -1.41E-14 | 2.06E-14 | 1.03E-14 | 1.52E-14 | -1.30E-14 |
| NF | B | -09871 | -0.9987 | 1.0007 | 0.9986 | 0.9992 | -1.0082 |
| | A | -0.9871 | -1.0168 | 0.9919 | 0.9861 | 0.9933 | -1.0067 |
| VAF (V) | B | 316 | 39.5 | -55.2 | -90.1 | -82.7 | 178 |
| | A | 231 | 44.3 | -93.4 | -120 | -113 | 67.2 |
| Icbo (A) | B | -4.10E-12 | -4.75E-13 | 6.91E-06 | 1.43E-06 | 1.33E-06 | -2.91E-12 |
| | A | -8.42E-11 | -1.13E-10 | 2.54E-09 | 6.62E-09 | 2.12E-09 | -2.58E-10 |
| ISC (A) | B | -5.28E-14 | -2.21E-15 | 1.41E-08 | 6.20E-09 | 4.51E-09 | -2.62E-14 |
| | A | -1.52E-12 | -1.35E-12 | 1.11E-11 | 5.30E-11 | 1.80E-11 | -6.25E-12 |
| NE | B | - | - | - | - | - | - |
| | A | -1.5426 | -1.9533 | 1.8488 | 1.7635 | 1.7684 | -1.9154 |
| ISE (A) | B | 0 | 0 | 0 | 0 | 0 | 0 |
| | A | -5.56E-13 | -5.15E-11 | 1.88E-11 | 1.06E-11 | 1.12E-11 | -6.20E-11 |

1 = BF621 -- PNP, HIGH VOLTAGE
2 = XN4401 -- PNP, ARRAY
4 = BCX70 -- NPN, SMALL SIGNAL
5 = XN2501 -- NPN, ARRAY, BASE COUPLED
6 = XN4501 -- NPN, ARRAY
7 = PN4888 -- PNP

\* THE RESULTING PARAMETERS FOR EACH TRANSISTOR TYPE ARE AVERAGES OF 3 TO 4 TESTED TRANSISTORS 02.16.00

FIG. 5

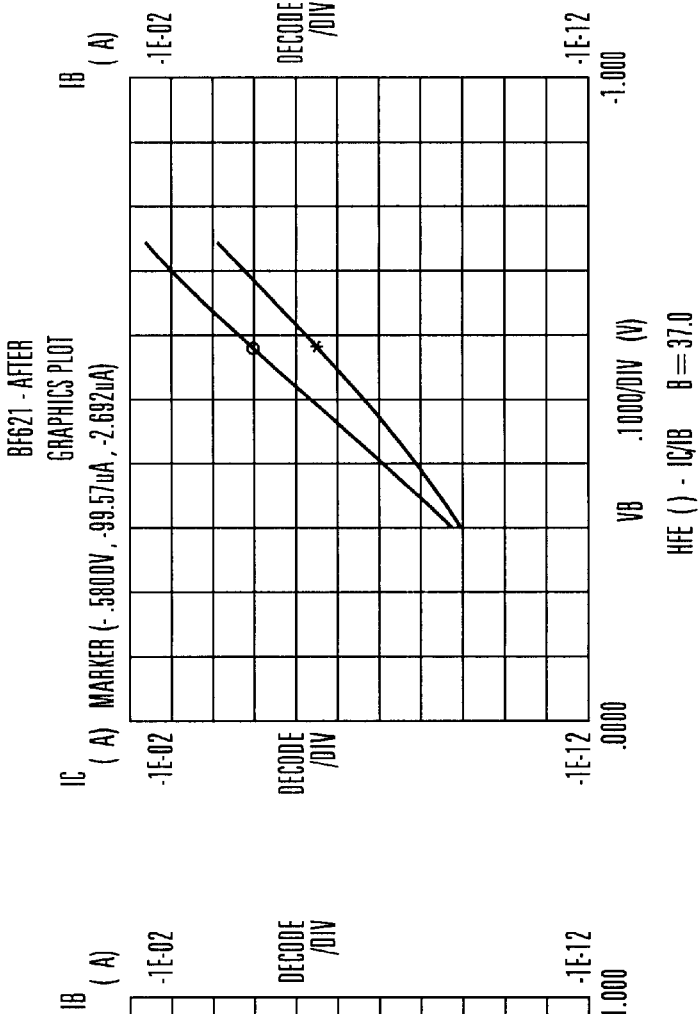
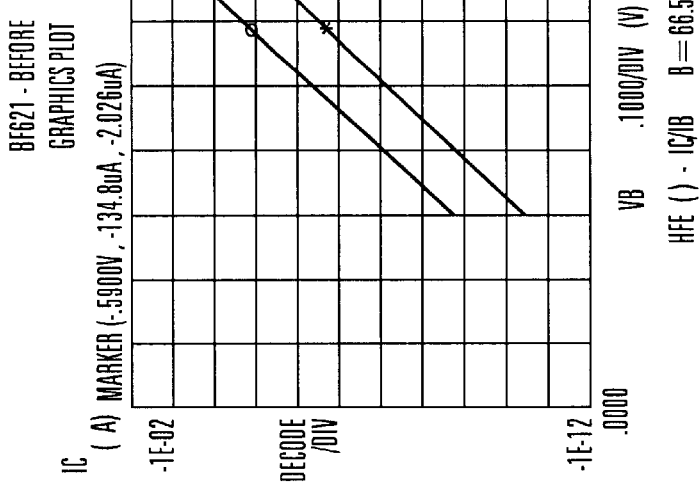

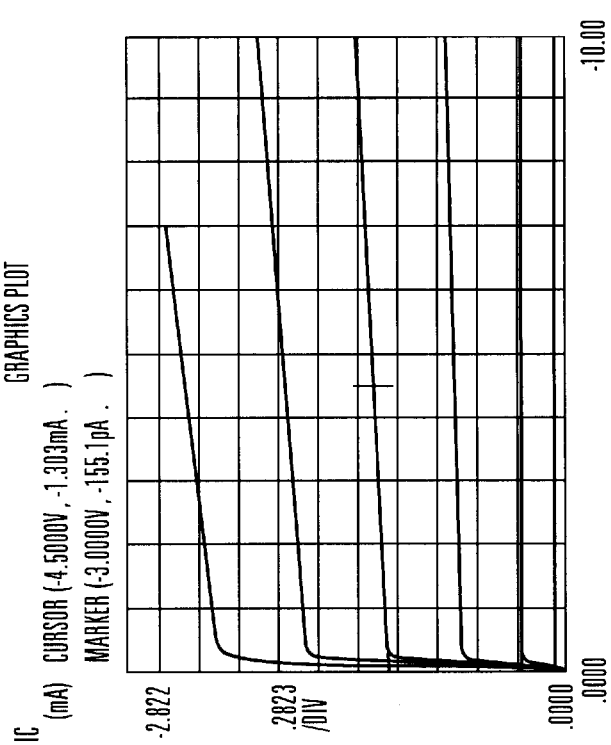
FIG. 8a
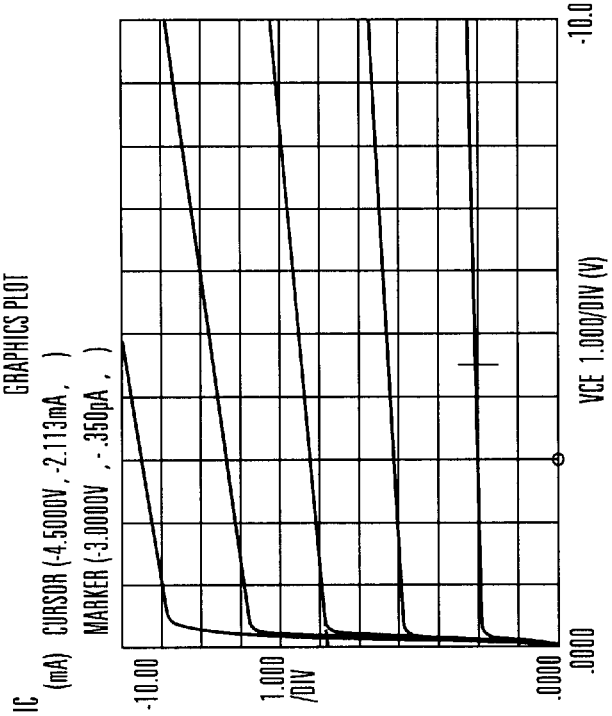
FIG. 8b
FIG. 8c

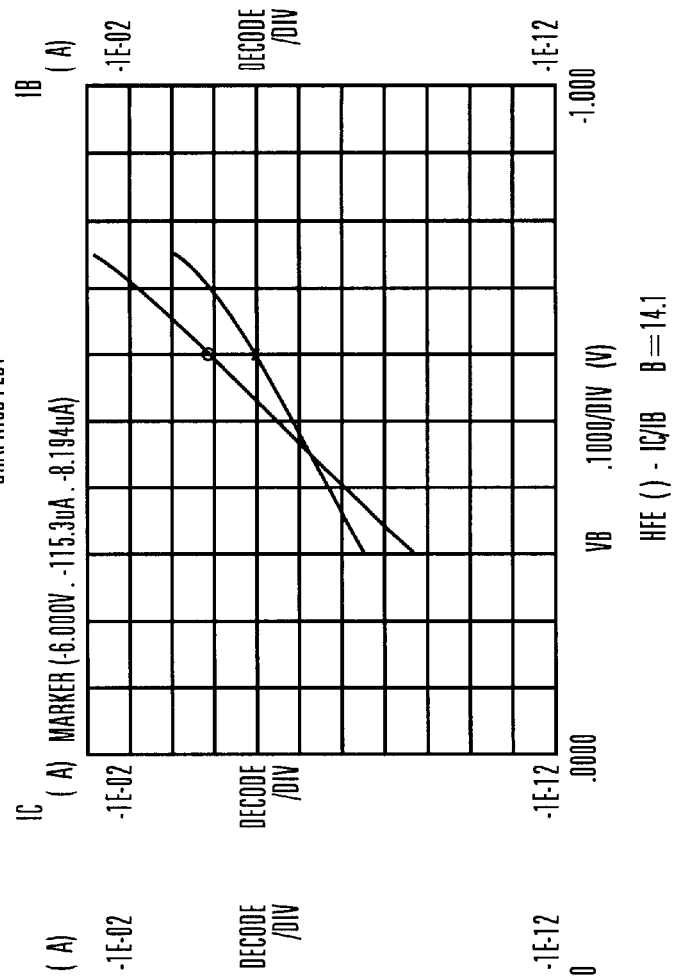
FIG. 9a
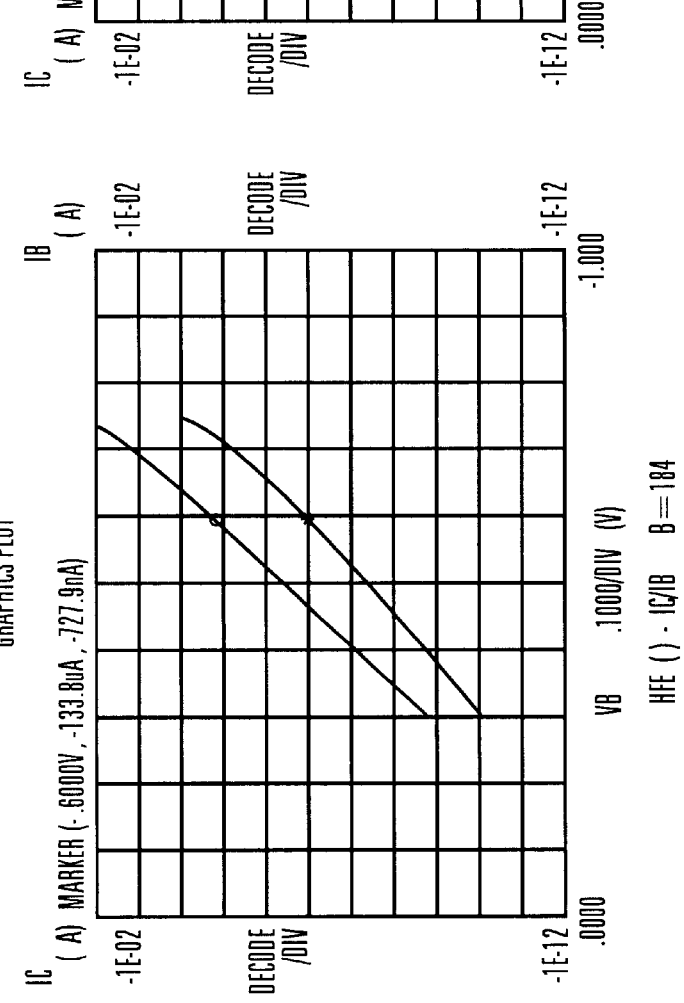
FIG. 9c
FIG. 9b

| TRANSISTOR | NUMBERS | HOW MANY TIMES STERLIZED |
|---|---|---|
| BF621 | 1-22 | 2 |
| BF621 | 22-80 | 1 |
| XN4401 | 1-10 | 2 |
| XN4401 | 11-20 | 1 |
| 2SC5019 | 1-9 | 2 |
| BCX70KCT | 1-21 | 2 |
| BCX70KCT | 22-36 | 1 |
| XN2501 | 1-10 | 2 |
| XN2501 | 11-20 | 1 |
| XN4501 | 1-10 | 2 |
| XN4501 | 11-20 | 1 |
| PN4888 | 1-20 | 2 |
| U401 | 1-20 | 2 |
| BSS138ZX | 1-10 | 2 |
| SST270 | 1-9 | 2 |
| GERMANIUM | 1-12 | 2 |
| GERMANIUM | 13-24 | 1 |
| BF720 | 1-10 | 1 |
| MPSA42 | 1-20 | 1 |
| MPSL51 | 1-20 | 1 |
| MPSA93 | 1-20 | 1 |
| 2N5401 | 1-20 | 1 |

FIG. 11

DEVICE AND METHOD FOR CIRCUIT PROTECTION DURING RADIATION STERILIZATION

FIELD OF THE INVENTION

This invention relates to circuit protection devices and methods, and in particular embodiments, to circuit protection devices and methods for use during radiation sterilization of devices containing electronic circuits.

BACKGROUND OF THE INVENTION

Over the years, sterilization of medical devices has become more important and difficult. At one time it was possible to sterilize most medical devices at the site of use, since the devices were relatively simple, such as reusable syringes, scalpels, scissors or the like. In addition, the medical devices were often used in a doctor's office, hospital, or the like, that included sophisticated sterilization equipment. Thus, the medical devices could be shipped for use without sterilization.

However, medical devices have changed considerably over the years. For instance, the devices are becoming more complicated and use many different materials, such that autoclaving, chemical sterilization, or the like, is no longer possible, since the processes would likely destroy the materials of the medical device or fail to reach areas not readily accessible after construction of the medical device. In addition, many medical devices are now being used in the home by patients, and these patients generally do not have the equipment necessary to perform the required sterilization. Thus, on-site sterilization has become difficult or impossible to perform at the site of use.

To overcome this drawback, most devices are now sterilized at the facility of manufacture, prior to shipment. Sterilization can be facilitated by sterilization of each component prior to assembly in a sterilized environment. However, additional sterilization is often required. Heat and chemical sterilization cannot always be used due to possible destruction of the various materials. To overcome issues of heat and chemical sterilization, radiation (including x-ray and electron beam) sterilization was developed to provide sterilization of a medical device once it was in its packaging. Thus, after sterilization, the device is shipped and stored in a sterilized environment until the medical device is to be used.

Although radiation sterilization has solved many sterilization issues, it is difficult to sterilize complicated devices containing electronic circuits, since the radiation has the capability to damage or destroy semiconductor circuit elements. One approach is to remove the circuits prior to sterilization, but this still raises issues of sterilization when the device is reassembled.

SUMMARY OF THE DISCLOSURE

It is an object of an embodiment of the present invention to provide an improved circuit protection device which obviates for practical purposes, the above mentioned limitations.

According to an embodiment of the invention, a circuit protection device for protection of sensitive components during high energy sterilization that includes a support substrate and a protective housing. The substrate supports the sensitive components. The protective housing is hermetically coupled to the support substrate to seal the sensitive components within the protective housing. Preferably, the protective housing stops high energy used in the high energy sterilization from damaging the sensitive components from a predetermined exposure level of high energy sterilization. In further embodiments, the circuit protection device includes a protective conductor that is coupled to the support substrate on a side which is opposite the protective housing to prevent high energy from entering the opposite side of the support substrate. The circuit protection device can also include an energy absorbing material contained within an area sealed by the protective housing to absorb high energy byproducts produced by the protective housing stopping the high energy used in the high energy sterilization. Preferably, the support substrate is a circuit board, and the sensitive elements are semiconductors. Also, the high energy sterilization is E-beam sterilization and the high energy are electrons, and the high energy byproducts are x-rays.

In particular embodiments, the energy absorbing material is an epoxy containing metal. Also, the protective housing and protective conductor are formed from a metal or other electrical conductor. For instance, the metal is selected from the group consisting essentially of titanium and aluminum.

In particular embodiments, the predetermined exposure level is above 2.0 Mrad. Alternatively, the predetermined exposure level is less than or equal to 5.0 Mrad, or the predetermined exposure level is above 0.5 Mrad.

In another embodiment of the present invention a circuit element for use in an electronic device includes a semiconductor structure. The semiconductor structure has been sterilized by a predetermined dosage of radiation. Also, the gain characteristics after radiation sterilization are reduced by less than a predetermined fraction of before radiation sterilization gain characteristics. In addition, after radiation sterilization the characteristics of collector current and base current as a function of base voltage change in a generally proportional relationship relative to each other. In preferred embodiments, the radiation sterilization is by gamma radiation. In particular embodiments, the circuit element is a transistor, a circuit array, or a PNP high voltage structure.

In further embodiments, the predetermined fraction of before radiation sterilization gain characteristics is 25%, 50%, 75%, or the like. The predetermined dosage of radiation is above 5 kGy, 10 kGy, 15 kGy, 20 kGy, 25 kGy, 30 kGy, or the like. In other embodiments, a ratio of the collector current and the base current, each as a function of the base voltage, has a magnitude greater than one for a predetermined operating range.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

FIG. 4 is a table describing various transistors and circuits tested in accordance with another embodiment of the present invention.

FIG. 5 is a table showing the before and after radiation treatment characteristics for the transistors and circuits, shown in FIG. 4, in accordance with embodiments of the present invention.

Figures 6A, 6B, 6C:
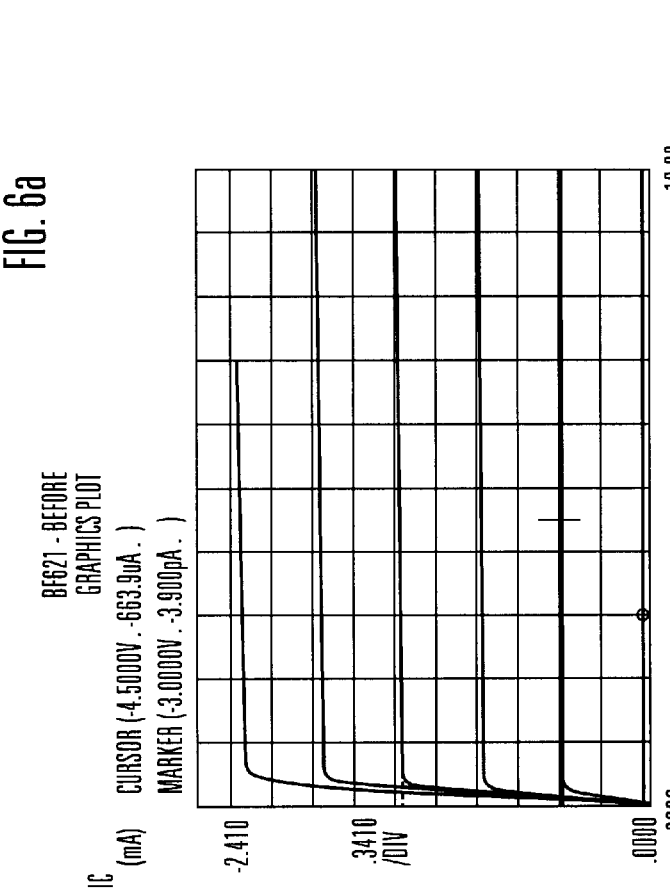
Figure 10A:
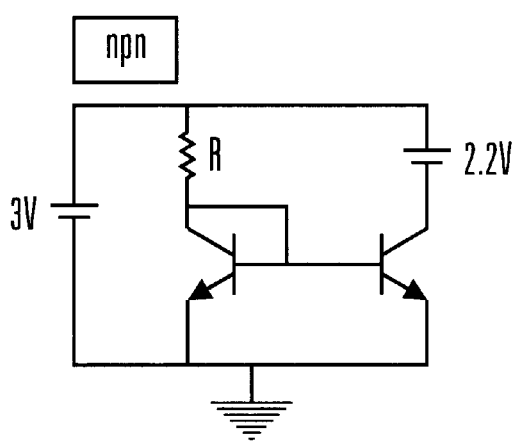
Figure 10B:
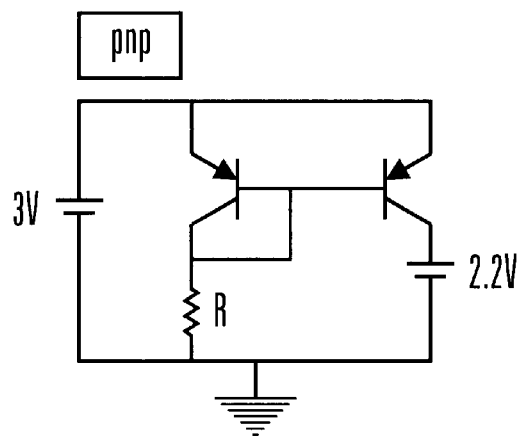
Figure 10C:
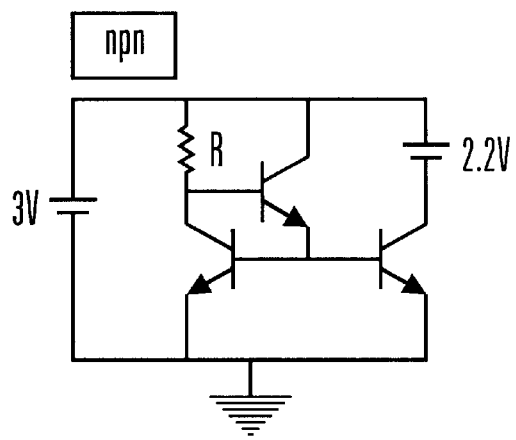
Figure 10D:
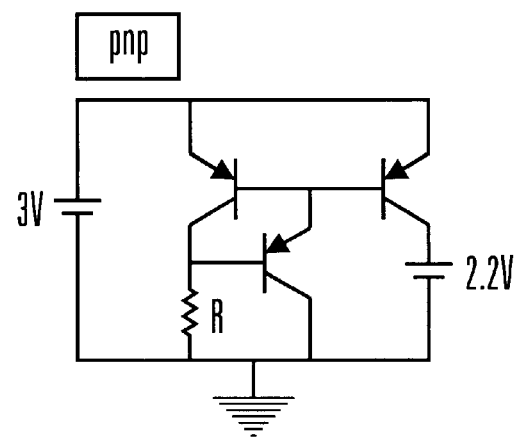
Figure 10E:
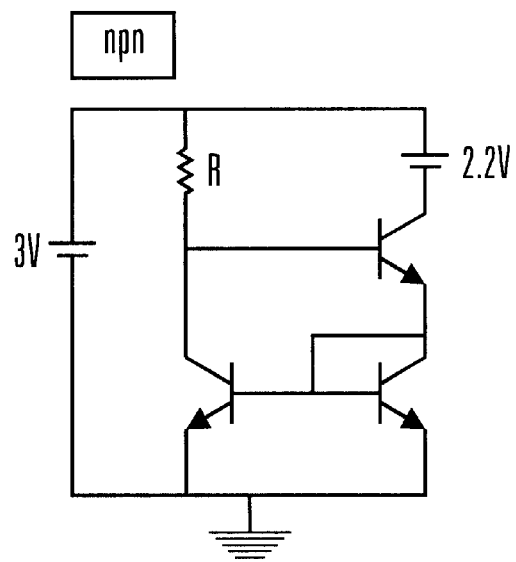
Figure 10F:
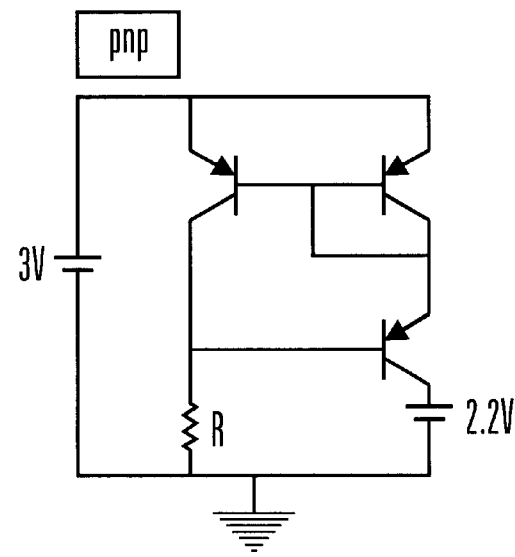

FIGS. 6a to 6c are directed to representative charts showing various B gain, or Beta, curves for collector current versus collector emitter voltage for a preferred transistor before and after radiation treatment, shown in FIGS. 4 and 5, in accordance with embodiments of the present invention.

FIGS. 7a to 7c are directed to representative charts showing characteristic curves, collector current versus base voltage and base current versus base voltage of a preferred transistor before and after radiation treatment, shown in FIGS. 4 and 5, in accordance with embodiments of the present invention.

FIGS. 8a to 8c are directed to representative charts showing various B gain, or Beta, curves for collector current versus collector emitter voltage for another transistor before and after radiation treatment, shown in FIGS. 4 and 5, in accordance with embodiments of the present invention.

FIGS. 9a to 9c are directed to representative charts showing characteristic curves, collector current versus base voltage and base current versus base voltage of another transistor before and after radiation treatment, shown in FIGS. 4 and 5, in accordance with embodiments of the present invention.

FIGS. 10a to 10f illustrate various circuit arrangements that may utilize transistors sterilized in accordance with embodiments of the present invention, as shown in FIGS. 4 and 5.

FIG. 11 is a table showing the various transistors and circuits sterilized and the number of times sterilization was performed in accordance with embodiments of the present invention.

DETAILED DESCRIPTION OF THE PREFERRED EMBODIMENTS

As shown in the drawings for purposes of illustration, the invention is embodied in a circuit protection device and method for use during E-beam sterilization to permit sterilization of a medical device containing semiconductor circuit elements. In preferred embodiments of the present invention, the circuit protection device forms a permanent part of a circuit board, which permits sterilization of the medical device and circuit board after final assembly. However, it will be recognized that further embodiments of the invention may be used to protect circuit elements that are sterilized prior to final assembly in a medical device. The circuit protection device is primarily adapted for use in medical device for external use. However, alternative embodiments may be used in medical devices to be placed internally within the patient or for both internal and external use. Preferred embodiments are for use with medication infusion devices. However, alternative embodiments may be used with other medical devices containing E-beam sensitive components. Preferred embodiments of the present invention are directed to protecting circuits during E-beam sterilization. However, other embodiments, may protect circuits during other sterilization techniques that utilize other energy sources, such as gamma ray, x-ray, proton beam, or the like.

Figure 2:
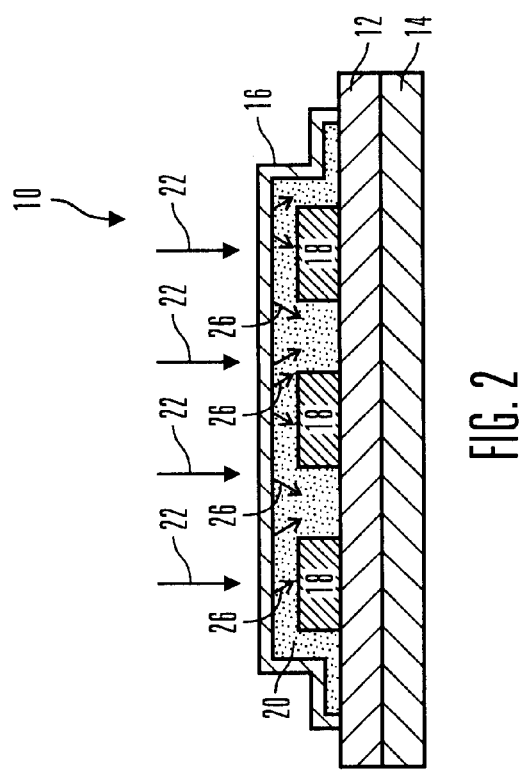
FIG. 2 is a partial cross-sectional diagram of the circuit protection device as shown along the line 2—2 in FIG. 1.
Figure 1:
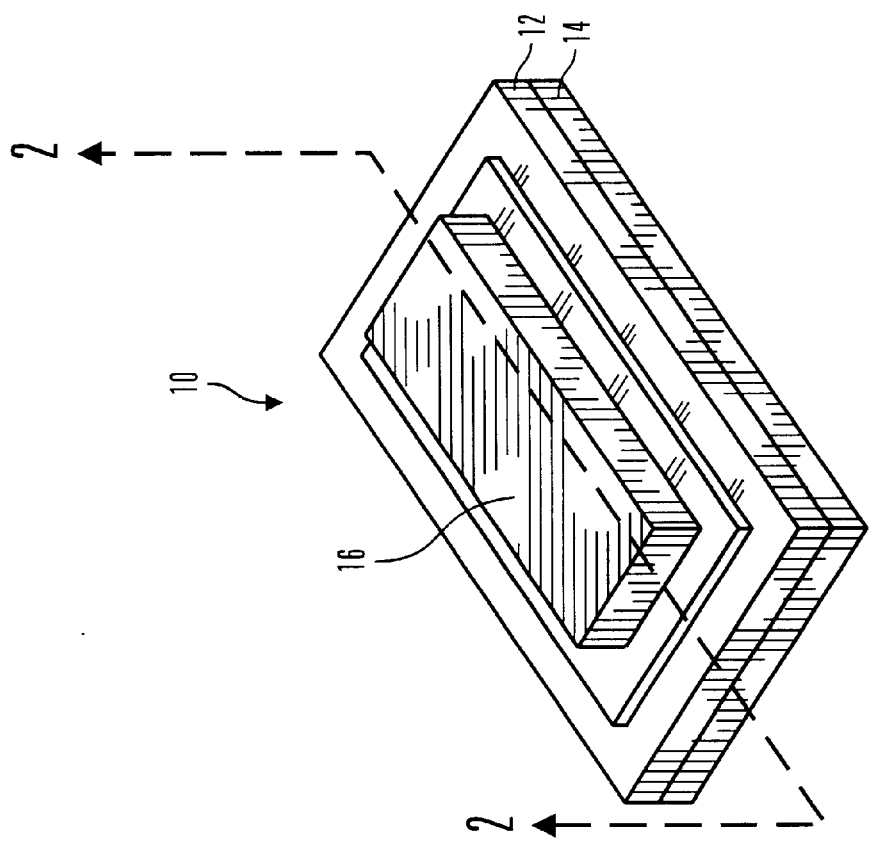
FIG. 1 is a perspective view of a circuit board that uses a circuit protection device in accordance with an embodiment of the present invention.
Figure 3:
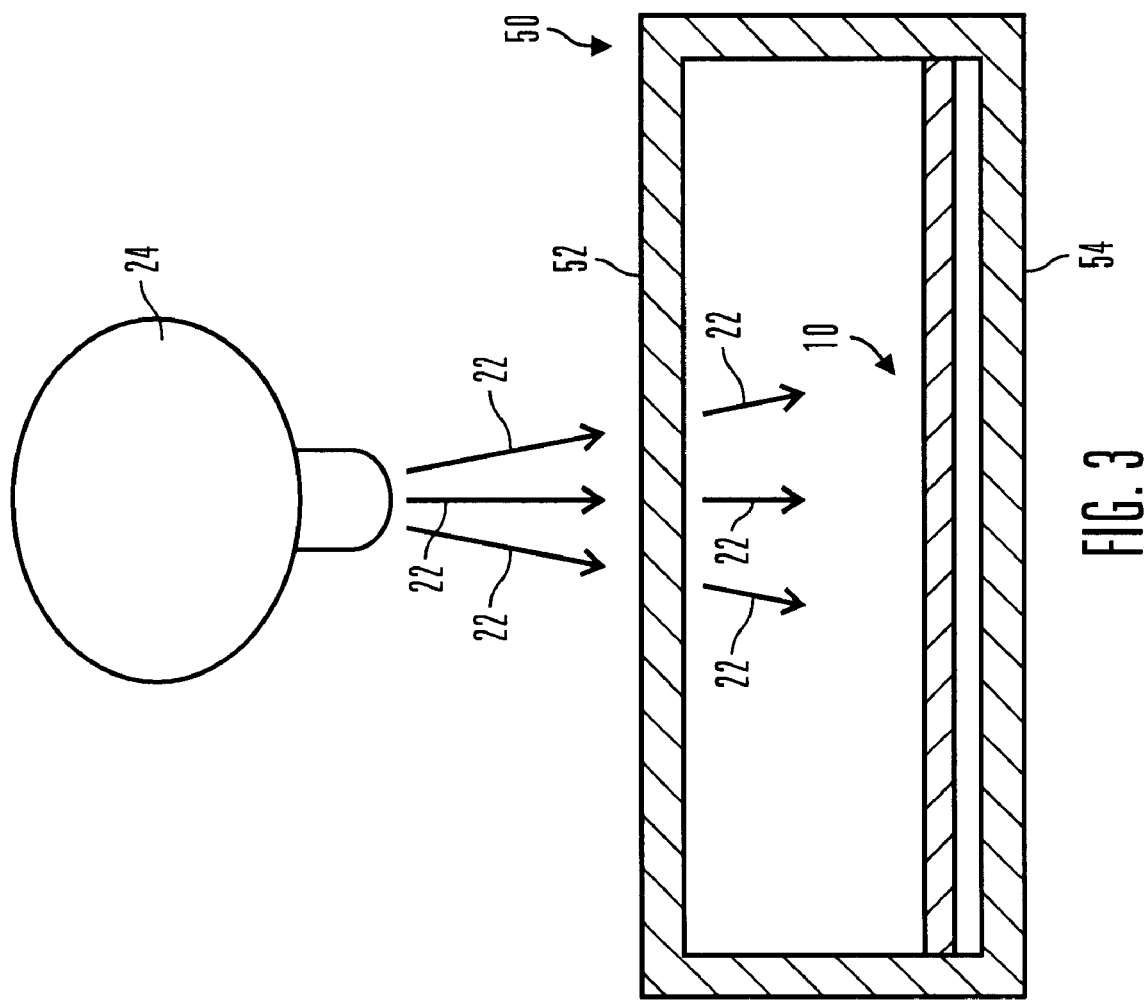
FIG. 3 is a cross-sectional diagram that shows a circuit board with a circuit protection device, as shown in FIGS. 1 and 2, that is contained in a medical device and is exposed to E-beam sterilization.

As shown in FIGS. 1–3, the circuit protection device 10 in accordance with a preferred embodiments of the present invention includes a circuit board 12 (or support substrate), a protective conductor 14 and a protective housing 16 to cover E-beam sensitive components 18 mounted on the circuit board 12. In preferred embodiments, the E-beam sensitive components are potted (or surrounded) with an energy absorbing substance 20 that further protects the E-beam sensitive components 18 mounted on the circuit board 12.

Preferred embodiments of the protective housing 16 are sealed the circuit board 12 to provide a hermetic seal. Thus, once the exterior of the protective housing 16 and the circuit board are sterilized, the entire component assembly is sterilized, since no contaminates inside the sealed environment around the E-beam sensitive components 18 can escape to effect the sterilized device. In preferred embodiments, the protective housing 16 is attached to the circuit board 12 using an adhesive, such as RTV, silicone based adhesives, epoxies, or the like. Also, if the energy absorbing material 20 is used and has adhesive properties, it may be used to secure the protective housing 16 and form the hermetic seal. In other embodiments, the protective housing 16 may be welded to the circuit board 12, or include a plastic liner that permits sonic welding of the protective housing 16 to the circuit board 14. In further embodiments, the protective housing 16 may be used with a gasket (not shown) and snapped in place or otherwise secured to the circuit board 12 to form a hermetic seal.

Preferably, the protective housing 16 is formed an electron stopping light metal such as aluminum or titanium. In alternative embodiments, other materials may be used that stop electrons or radiation, such as silver, gold, lead, tantalum, or the like or other electrically conductive materials. Preferably, the protective housing 16 is formed from a single sheet of stamped metal to facilitate assembly and to reduce cost. However, alternative embodiments may use other structures, such as cast metals, laminates, or the like. In addition, the protective conductor 14 should be formed of a similar electron stopping material to prevent electrons from passing through the back of the circuit board 12 to the E-beam sensitive components 18.

Preferred embodiments of the protective housing 16 and protective conductor 14 have a thickness that is sufficient to withstand electron beam sterilization and stop the electrons with a preferred single dose of 2.0 Mrads (or 20 kGy). However, in alternative embodiments, smaller dose levels may be used if sufficient sterilization may be achieved at the lower dose, such as for example 0.5 Mrads (5 kGy). Larger doses may also be used, if the protective housing 16 and protective conductor 14 (as well as other medical device components - not shown) are selected and assembled to withstand doses up to 5.0 Mrads (50 kGy). The circuit protection device 10 materials are carefully selected with regard to protective housing materials, circuit board materials, electrodes, any membranes, chemistry, lubricants, and the packaging materials, and manufacturing tolerances to assure the ability to withstand electron beam sterilization and the continued proper operation of the E-beam sensitive components 18 after sterilization.

In operation, as shown in FIGS. 2 and 3, the protective housing 16 stops the electrons in the E-beam 22 from an E-beam source 24 from reaching and impinging on the E-beam sensitive components 18 after passing through the walls 52 of a medical device 50. In addition, the protective conductor 14 prevents electrons in the E-beam 22 from reflecting off of a back wall 54 in the medical device 50 and damaging the E-beam sensitive components 18 by passing through the back of the circuit board 12. Thus, the structure of the of circuit protection device 10 formed by the circuit board 12, the protective conductor 14 and the protective housing forms a small Faraday cage to protect the enclosed E-beam sensitive components 18 from damaging electrons during the sterilization procedure.

Light metals, as discussed above, are particularly well adapted to stopping electrons in E-beams 22. However, a drawback to the use of light metals is that they often produce x-rays 26 (see FIG. 2) as a byproduct from the stopping of the electrons in the E-beams 22. Therefore, to protect the E-beam sensitive components 18, the interior area under the protective housing 16 is filled with an energy absorbing material 20 that is particularly well suited for absorbing x-rays, or electron stopping energy byproducts. In preferred embodiments, the energy absorbing material is an epoxy that contains a metal to stop and absorb the x-rays. Any such compound should be selected to avoid interfering with any electrical operation of the E-beam sensitive components 18. In alternative embodiments, the energy absorbing material is a liner (not shown) in a laminate structure forming the protective conductor 14 and protective housing 16, such as lead, or the like, that stops and absorbs x-rays. In further alternatives, other energy absorbing materials may be used.

Preferred embodiments of the E-beam sensitive components 18 are semiconductor devices, such as microprocessors, RAMs, ROMS, flash memory, or the like. However, alternative embodiments, may include other E-beam sensitive components, such as temperature sensors, antennas, power sources, batteries, or the like. If the E-beam sensitive components 18 generate heat (or need to conduct heat), then it is preferred that any energy absorbing material 20 act as a conductor to maintain temperature equilibrium within the medical device 50.

FIGS. 4 through 11 are directed to another embodiment of the present invention, where specific transistor and circuits are selected based upon their ability to maintain functionality with minimized loss of gain characteristics after radiation sterilization. A study was conducted to determine which transistors and circuit types are most acceptable for withstanding gamma radiation sterilization. Transistors and circuits listed and numbered in FIGS. 4 and 5 were tested prior to and then after gamma radiation to determine the characteristics of the transistors and circuits. The test exposed the transistors and circuits to a total radiation dose of 30.9 to 33.3 kGy. In each of the tests, 10–20 samples were exposed to the radiation and samples were tested before and after sterilization. In further embodiments, the transistors and circuits were sterilized a second time at a dosage level of 30.8 to 32.4 kGy. FIG. 11 lists the components tested, the number of units tested, and how many times each unit was sterilized. In alternative embodiments, larger or smaller does may be used and/or a different number of sterilizations may be performed with the selection being dependent on the transistor or circuit to be sterilized, type of medical device, number of times the medical device will be used, and environment in which the medical device will be used. In addition, other circuit components, such as Zener diodes, LEDs, or the like may be identified and used in these embodiments.

FIG. 5 is a table showing the before and after radiation treatment characteristics for samples of the transistors and circuits in accordance with embodiments of the present invention. The table shows that BF (peak) and B@~100 uA is reduced by a substantially small amount of loss due to radiation if the proper transistor or circuit is chosen. For instance, the preferred embodiment identified that PNP, high voltage transistors or circuits have the lowest loss of gain and deterioration of other characteristics. Hence, selecting the proper transistor or circuit facilitates the ability to design a medical device that will withstand gamma radiation sterilization processes. If the gains are reduced and the characteristics degrade in a predictable manner, or in a way that does not cause unexpected results to occur, the medical device can be safely sterilized. All test results were verified for predictability by modeling in the SPICE program and then checking the SPICE program results against the actual obtained results. Typical circuits in which various radiation sterilized transistors and circuits may be used are shown in FIGS. 10a to 10f.

FIGS. 6a to 6c are directed to representative charts showing various B (beta or gain) curves, collector current versus collector-emitter voltage as a function of base currents for a preferred transistor before and after radiation treatment in accordance with an embodiment of the present invention. This chart shows that for the transistor of test group 1 in FIG. 5, the gain was reduced in a generally proportional manner. FIGS. 7a to 7c are directed to representative charts of characteristic curves, showing the relationship of collector current and base current, each as a function of base voltage, of a preferred transistor before and after radiation treatment in accordance with an embodiment of the present invention. A key aspect of FIG. 7c is that the gain of the transistor as a function of base voltage before the radiation treatment has roughly the same proportionality (on a logarithmic graph) after radiation treatment. The graphed relationship shows a similar slope, which implies a lowering of gain, but without a significant increase in leakage current at the base emitter junction of the device. The gain after sterilization treatment is therefore shifted lower, but proportionately. This implies that the transistor will work in a manner consistent with its behavior prior to radiation sterilization. For instance, a ratio of collector current to base current (hFe or gain), each as a function of base voltage, of the expected, normal operating range of circuit will yield a ratio having a magnitude greater than one—the slopes will not intercept in the expected operating range. The operating range being determined by the type of medical device, length of operation, operating environment and safety margin required to avoid malfunctions. Thus, the electronics of the medical device may be designed to utilize a gain with the expected and predictable change after the sterilization treatment. This finding means that a medical device circuit without feedback control can be designed to work predictably with components having these characteristics. Also, for circuits using feedback control, circuits in medical devices in which the components are used can be designed to work even with the gain reduction after sterilization treatment. Further, it should be understood that the graphs show a general relationship on the characteristics, which may be used to tune the radiation sterilization process or circuit design to achieve desired performance characteristics in the radiation sterilized medical device.

Conversely, FIGS. 8a to 8c are directed to representative charts showing various B (Beta, or gain) curves, collector current versus collector-emitter voltage as a function of base current, for another transistor before and after radiation treatment in accordance with an embodiment of the present invention. The gain of this transistor in test group 2 shows that the gain changed in a non-proportional manner (on a logarithmic graph) for some values of base current. FIGS. 9a to 9c are directed to representative charts of characteristic curves, collector current and base current, each as a function of base voltage. This implies leakage at the semiconductor junction in the device, and gain non-linearity, especially at low base voltages, where base currents represent a larger proportion of the total collector current. In this instance, the component would not change predictably after the sterilization treatment, and would be far less suitable as a component choice for the circuit in a medical device. For instance, a ratio of collector current to base current (hFe or gain), each as a function of base voltage, of the expected, normal operating range of circuit will yield a ratio having a magnitude less than or equal to one—the slopes will intercept at some point within the expected operating range. The operating range being determined by the type of medical device, length of operation, operating environment and safety margin required to avoid malfunctions.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A circuit protection device for protection of sensitive components during high energy radiation sterilization, the device comprising;
    a support substrate that supports the sensitive components;
    a protective housing that is hermetically coupled to the support substrate to seal the sensitive components within the protective housing;
    wherein the protective housing stops high energy used in the high energy radiation sterilization from damaging the sensitive components from a predetermined exposure level of high energy sterilization; and
    an energy absorbing material contained within an area sealed by the protective housing to absorb high energy byproducts produced by the protective housing stopping the high energy used in the high energy sterilization.

2. The device according to claim 1, further including a protective conductor coupled to the support substrate on a side opposite the protective housing to prevent high energy from entering the side of the support substrate.

3. The device according to claim 2, wherein the support substrate is a circuit board, and wherein the sensitive elements are semiconductors.

4. The device according to claim 2, wherein the high energy sterilization is E-beam sterilization and the high energy are elections.

5. The device according to claim 4, wherein the high energy byproducts are x-rays.

6. The device according to claim 5, wherein the energy absorbing material is an epoxy containing meterial.

7. The device according to claim 3, wherein the predetermined exposure level is above 2.0 Mrad.

8. The device according to claim 3, wherein the predetermined exposure level is less than or equal to 5.0 Mrad.

9. The device according to claim 3, wherein the predetermined exposure level is above 0.5 Mrad.

10. The device according to claim 2, wherein the protective housing and protective conductor are formed from a metal.

11. The device according to claim 10, wherein the metal is selected from the group consisting essentially of titanium and aluminum.

12. The device according to claim 1, wherein the protective housing is formed from a metal.

13. The device according to claim 12, wherein the metal is selected from the group consisting essentially of titanium and aluminum.

14. A circuit element for use in an electronic device, the circuit element comprising:
    a semiconductor structure,
    wherein the semiconductor structure has been sterilized by a predetermined dosage of radiation,
    wherein gain characteristics after radiation sterilization are reduced by less than a predetermined fraction of before radiation sterilization gain characteristics, and
    wherein after radiation sterilization, characteristics of a collector current and a base current for a given base voltage change in a generally proportional relationship relative to each other.

15. The circuit element in accordance with claim 14, wherein the radiation sterilization is by gamma radiation.

16. The circuit element in accordance with claim 14, wherein the predetermined fraction of before radiation sterilization gain characteristics is 25%.

17. The circuit element in accordance with claim 14, wherein the predetermined fraction of before radiation sterilization gain characteristics is 20%.

18. The circuit element in accordance with claim 14, wherein the predetermined fraction of before radiation sterilization gain characteristics is 75%.

19. The circuit element in accordance with claim 14, wherein the predetermined dosage of radiation is above 5 kGy.

20. The circuit element in accordance with claim 14, wherein the predetermined dosage of radiation is above 10 kGy.

21. The circuit element in accordance with claim 14, wherein the predetermined dosage of radiation is above 15 kGy.

22. The circuit element in accordance with claim 14, wherein the predetermined dosage of radiation is above 20 kGy.

23. The circuit element in accordance with claim 14, wherein the predetermined dosage of radiation is above 25 kGy.

24. The circuit element in accordance with claim 14, wherein the predetermined dosage of radiation is above 30 kGy.

25. The circuit element in accordance with claim 14, wherein the circuit element is a transistor.

26. The circuit element in accordance with claim 14, wherein the circuit element is a circuit array.

27. The circuit element in accordance with claim 14, wherein a ratio of collector current to base current, each as a function of the base voltage, has a magnitude greater than one over a predetermined expected operating image.

28. The circuit element in accordance with claim 14, wherein the semiconductor structure is a PNP high voltage structure.

* * * * *